US008645158B2

(12) United States Patent
Lancaster et al.

(10) Patent No.: US 8,645,158 B2
(45) Date of Patent: *Feb. 4, 2014

(54) DISPLAYING CLINICAL PREDICTED LENGTH OF STAY OF PATIENTS FOR WORKLOAD BALANCING IN A HEALTHCARE ENVIRONMENT

(75) Inventors: Brian J. Lancaster, Shawnee, KS (US); Jill Hagel, Lenexa, KS (US)

(73) Assignee: Cerner Innovation, Inc., Kansas City, KS (US)

( * ) Notice: Subject to any disclaimer, the term of this patent is extended or adjusted under 35 U.S.C. 154(b) by 291 days.

This patent is subject to a terminal disclaimer.

(21) Appl. No.: 12/647,850

(22) Filed: Dec. 28, 2009

(65) Prior Publication Data

US 2010/0100394 A1    Apr. 22, 2010

Related U.S. Application Data

(63) Continuation of application No. 11/315,051, filed on Dec. 22, 2005, now Pat. No. 7,664,659.

(51) Int. Cl.
*G06Q 50/00* (2012.01)
(52) U.S. Cl.
USPC ............................................................ 705/2
(58) Field of Classification Search
USPC ................... 705/2–4; 600/300–301
See application file for complete search history.

(56) References Cited

U.S. PATENT DOCUMENTS

| 5,018,067 | A | * | 5/1991 | Mohlenbrock et al. | 600/300 |
| 5,195,031 | A | * | 3/1993 | Ordish | 705/37 |
| 7,047,158 | B2 | * | 5/2006 | Roba et al. | 702/182 |
| 7,333,887 | B2 | * | 2/2008 | Baiada et al. | 701/120 |
| 2004/0243433 | A1 | * | 12/2004 | Akin et al. | 705/2 |
| 2005/0177396 | A1 | * | 8/2005 | Gottlieb et al. | 705/2 |
| 2007/0041623 | A1 | * | 2/2007 | Roehrig et al. | 382/128 |

OTHER PUBLICATIONS

"Q3 2005 PXRE Group Ltd. Earnings Conference Call—Final"; Fair Disclosure Wire, Oct. 28, 2005. From Dialog File 15 (ABI/Inform®).*
"The Integrated Inpatient Management Model—A New Approach to Clinical Practice" McMahon et al.; Annals of Internal Medicine, vol. 111 No. 4 pp. 318-326, Aug. 15, 1989.*
"The Evaluation of Screening Methods to Identify Medically Unnecessary Hospital Stay for Patients with Pneumonia"; Hartz et al.; International Journal for Quality in Healthcare, vol. 8 No. 1, pp. 3-11, 1996.*

* cited by examiner

*Primary Examiner* — John Pauls
(74) *Attorney, Agent, or Firm* — Shook Hardy & Bacon LLP

(57) ABSTRACT

A computerized system method for displaying a predicted length of stay and actual length of stay in an inpatient healthcare facility for a patient is provided. A predicted length of stay and an actual length of inpatient stay in a healthcare facility for a patient are accessed. The predicted length of stay and the actual length of inpatient stay for the patient are displayed concurrently.

7 Claims, 4 Drawing Sheets

500

CASE MANAGER WORK LIST

| PATIENT | PATIENT ID | ACTUAL LOS | PREDICTED LOS | DIFF. |
|---|---|---|---|---|
| DOE, JANE | 001 | 2 | 3 | 1 |
| SMITH, JOHN | 002 | 2 | 4 | 2 |
| JACKSON, CHARLIE | 003 | 1 | 4 | 3 |

502 / 504 / 506 / 508

500

CASE MANAGER WORK LIST

| PATIENT | PATIENT ID | ACTUAL LOS | PREDICTED LOS | DIFF. |
|---|---|---|---|---|
| DOE, JANE | 001 | 2 | 3 | 1 |
| SMITH, JOHN | 002 | 2 | 4 | 2 |
| JACKSON, CHARLIE | 003 | 1 | 4 | 3 |

FIG. 5.

DISPLAYING CLINICAL PREDICTED LENGTH OF STAY OF PATIENTS FOR WORKLOAD BALANCING IN A HEALTHCARE ENVIRONMENT

CROSS-REFERENCE TO RELATED APPLICATIONS

This is a continuation application of U.S. application Ser. No. 11/315,051, filed on Dec. 22, 2005.

STATEMENT REGARDING FEDERALLY SPONSORED RESEARCH OR DEVELOPMENT

Not applicable.

BACKGROUND

Oftentimes, an inpatient healthcare facility is reimbursed for treatment of patients based on a prospective payment system. As healthcare costs began to escalate, in 1983, the retrospective payment system for the Medicare program was replaced by a prospective payment system. The prospective payment system pays for acute hospital care based on the expected costs, rather than accrued charges.

Each patient discharged from a hospital setting is categorized into a billing group called a Diagnosis Related Group (DRG). The International Classification of Diseases, Ninth Revision, and Clinical Modifications (ICD-9-CM) is used to implement the DRG prospective payment system. ICD-9-CM is a diagnostic dictionary allowing diseases, symptoms, health problems and procedures to be classified and coded. The coded data elements are utilized to determine the DRG for a patient. The inpatient facility is reimbursed a predetermined amount for all services, no matter the length of stay or amount of resources used by the patient. Thus, a given inpatient facility may be paid the same for a patient with congestive heart failure who has had an inpatient stay of three days and a patient with congestive heart failure who has stayed for five days consuming more resources.

Current systems do not determine the predicted length of stay for a patient when the patient is admitted or during the patient's stay. The systems also do not display the current length of stay for the patient along with a predicted length of stay. As such, caregivers and administrators cannot easily view which patients are nearing discharge or determine which patients may require an extended stay for which utilization review is needed based on a predicted length of stay.

SUMMARY

In one embodiment, a computerized method for displaying a predicted length of stay and actual length of stay in an inpatient healthcare facility for a patient is provided. A predicted length of stay and an actual length of inpatient stay in a healthcare facility for a patient are accessed. The predicted length of stay and the actual length of inpatient stay for the patient are displayed concurrently.

In another embodiment, a user interface embodied on at least one computer readable medium for simultaneously displaying a predicted length of stay for a patient and an actual length of stay for a patient in an inpatient healthcare setting is provided. The user interface comprises a first display area configured to display a current length of stay for a patient in an inpatient healthcare facility and a second display area configured to display a predicted length of stay for the patient in the inpatient healthcare facility.

In yet another embodiment, a computerized method of determining a predicted length of stay in an inpatient healthcare facility for a patient is provided. Patient data for a current patient is received and historical data for previously treated patients is accessed. The patient data and historical data are utilized to determine a predicted length of inpatient stay for the patient and the predicted length of stay for the patient is displayed.

BRIEF DESCRIPTION OF THE SEVERAL VIEWS OF THE DRAWINGS

The present invention is described in detail below with reference to the attached drawing figures, wherein:

FIG. 5 is an exemplary screen displaying a case manager work list in accordance with an embodiment of the present invention.

DETAILED DESCRIPTION

Embodiments of the present invention are directed to a system and method for utilizing predicted length of stay for a patient for workload balancing in accordance with embodiments of the present invention.

Having briefly provided an overview of the present invention, embodiments of the invention will be discussed with reference to FIGS. 1-5.

Figure 1:
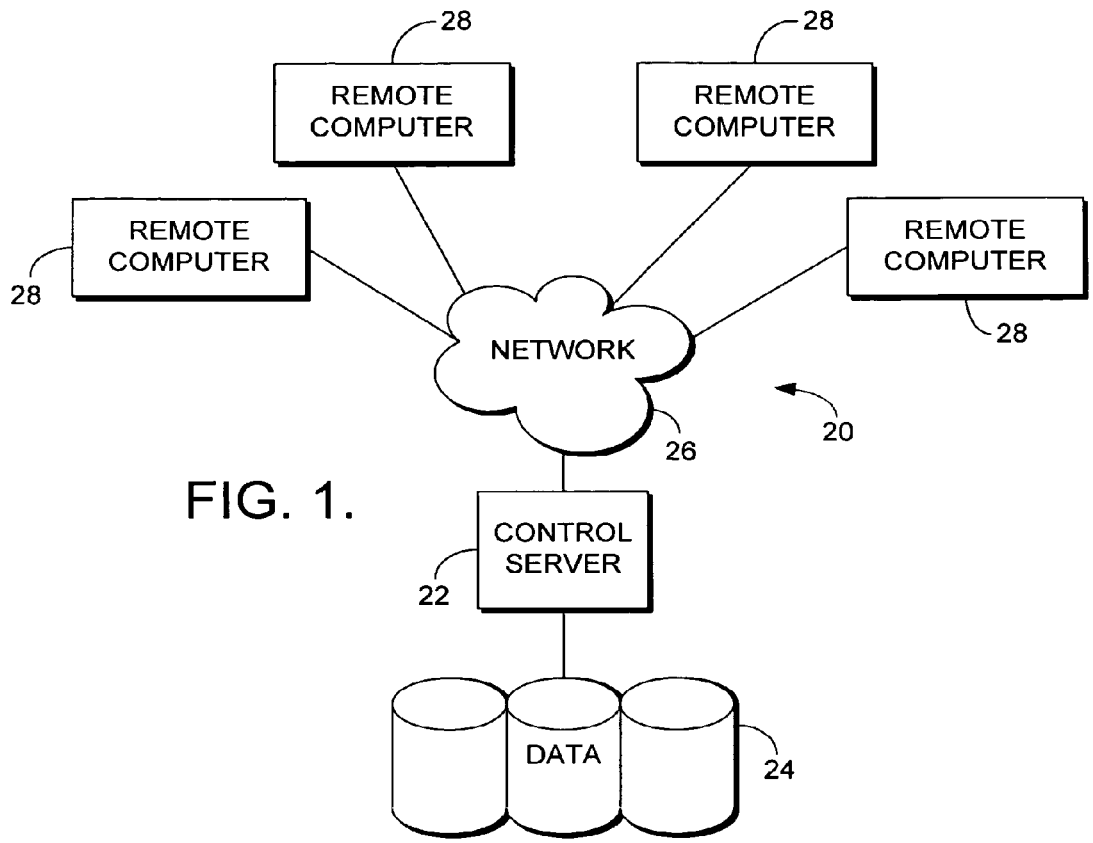
FIG. 1 is a block diagram illustrating a system for use with an embodiment of the present invention.

With reference to FIG. 1, an exemplary medical information system for implementing embodiments of the invention includes a general purpose-computing device in the form of server 22. Components of server 22 may include, but are not limited to, a processing unit, internal system memory, and a suitable system bus for coupling various system components, including database cluster 24 to the control server 22. The system bus may be any of several types of bus structures, including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

Server 22 typically includes therein or has access to a variety of computer readable media, for instance, database cluster 24. Computer readable media can be any available media that can be accessed by server 22, and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information, such as computer readable instructions, data structures, program modules or other data. Computer storage media includes, but is not limited to, RAM, ROM, EEPROM, flash memory or other memory technology, CD-ROM, digital versatile disks (DVD), or other optical disk storage, magnetic cassettes, magnetic tape, magnetic disk storage, or other magnetic storage devices, or any other medium which can be used to store the desired information and which can be accessed by server 22. Communication media typically embodies computer readable instructions, data structures, program modules, or other data in a modulated data signal, such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media, such as a wired network or direct-wired connection, and wireless media such as acoustic, RF, infrared and other wireless media. Combinations of any of the above should also be included within the scope of computer readable media.

The computer storage media, including database cluster 24, discussed above and illustrated in FIG. 1, provide storage of computer readable instructions, data structures, program modules, and other data for server 22.

Server 22 may operate in a computer network 26 using logical connections to one or more remote computers 28. Remote computers 28 can be located at a variety of locations in a medical or research environment, for example, but not limited to, clinical laboratories, hospitals, other inpatient settings, a clinician's office, ambulatory settings, medical billing and financial offices, hospital administration, veterinary environment and home health care environment. Clinicians include, but are not limited to, the treating physician, specialists such as surgeons, radiologists and cardiologists, emergency medical technologists, discharge planners, care planners, physician's assistants, nurse practitioners, nurses, nurse's aides, pharmacists, dieticians, microbiologists, laboratory experts, laboratory scientist, laboratory technologists, genetic counselors, researchers, veterinarians and the like. The remote computers may also be physically located in non-traditional medical care environments so that the entire health care community is capable of integration on the network. Remote computers 28 may be a personal computer, server, router, a network PC, a peer device, other common network node or the like, and may include some or all of the elements described above relative to server 22. Computer network 26 may be a local area network (LAN) and/or a wide area network (WAN), but may also include other networks. Such networking environments are commonplace in offices, enterprise-wide computer networks, intranets and the Internet. When utilized in a WAN networking environment, server 22 may include a modem or other means for establishing communications over the WAN, such as the Internet. In a networked environment, program modules or portions thereof may be stored in server 22, or database cluster 24, or on any of the remote computers 28. For example, and not limitation, various application programs may reside on the memory associated with any one or all of remote computers 28. It will be appreciated that the network connections shown are exemplary and other means of establishing a communications link between the computers may be used.

A user may enter commands and information into server 22 or convey the commands and information to the server 22 via remote computers 28 through input devices, such as keyboards, pointing devices, commonly referred to as a mouse, trackball, or touch pad. Other input devices may include a microphone, scanner, or the like. Server 22 and/or remote computers 28 may have any sort of display device, for instance, a monitor. In addition to a monitor, server 22 and/or computers 28 may also include other peripheral output devices, such as speakers and printers.

Although many other internal components of server 22 and computers 28 are not shown, those of ordinary skill in the art will appreciate that such components and their interconnection are well known. Accordingly, additional details concerning the internal construction of server 22 and computer 28 need not be disclosed in connection with the present invention. Although the method and system are described as being implemented in a LAN operating system, one skilled in the art would recognize that the method and system can be implemented in any system.

Figure 2:
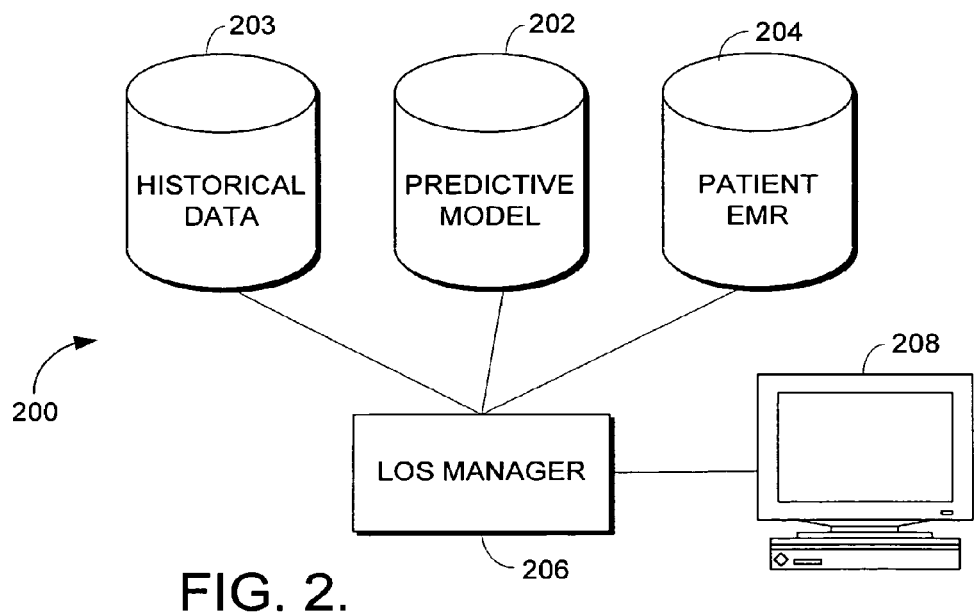
FIG. 2 is a block diagram illustrating components of a system for displaying a predicted length of stay for a patient in a healthcare environment in accordance with an embodiment of the present invention.

With reference to FIG. 2, a block diagram is provided illustrating an exemplary architecture 200 for processing and displaying predicted length of stays in accordance with an embodiment of the present invention. As shown in FIG. 2, a length of stay (LOS) manager 206 may be provided to coordinate, among other things, the calculation and dissemination of a patient's predicted length of stay. The patient's length of stay refers to the acute care stay, measured in total days, for inpatient admission to healthcare facility.

One or more predictive models may be maintained in an associated computerized database 202. The one or more predictive models may include a variety of statistical techniques for identifying a possible future outcome. For example, statistical techniques such as multiple algorithms, linear regression, partial least squares and logistic regression may be applied to stored historical data for a variety of patients. An exemplary predictive model that may be utilized for determining the predicted length of stay for a patient is described in the article by Jimenez, Rosa, et al. entitled "Difference between observed and predicted length of stay as an indicator of inpatient care inefficiency" *International Journal for Quality in Health Care* 1999; Volume 11, No. 5, pp. 375-384, the entirety of which is hereby incorporated by reference.

Historical data for a variety of patients to be utilized by the predictive model stored in database 202 are stored in associated computerized database 203. Predictive modeling data may include statistical techniques and historical data for variety of previously treated patients. The historical data may be for a variety of previously treated patients and include ICD-9 admission codes for each of the patients, age of each of the patients, location or region for each of the patients, actual length of stay for each of the patients and other clinical information such as ordered procedures, treating physician names, outcomes and other clinical data related to treatment of the patient. The historical data may be accessed from electronic medical records for the patients, community health records or other databases known to those of skill in the art.

As shown in FIG. 2, the length of stay manager 206 communicates with databases such as the predictive modeling database 202, historical database 203, the patient's electronic medical record 204 and display device 208. The display device 208 may include a computing device, such as a remote computer 28 of FIG. 1, for communicating with the length of stay manager 206. In addition, communication between the length of stay manager 206 and the display device may be via one or more networks which may comprise one or more wide area networks (WANs) and one or more local area networks (LANs), as well as public networks, such as the Internet, and one or more private networks. In some embodiments, a native clinical computing system may be utilized to communicate with the length of stay manager 206.

Figure 3:
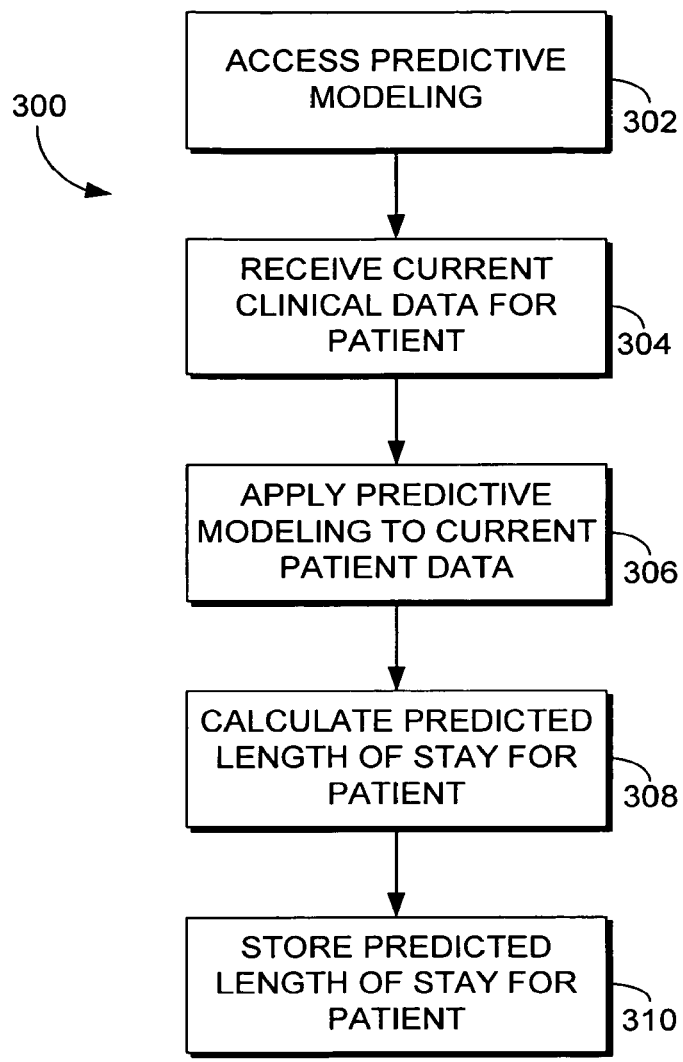
FIG. 3 is a flow diagram illustrating a method for calculating and storing a predicted length of stay for a patient in accordance with an embodiment of the present invention.

Referring next to FIG. 3, a method 300 of calculating and storing a predicted length of stay for a patient is shown. At step 302 predictive modeling data is accessed from a database such as database 202 of FIG. 2. At step 304, current clinical data for a patient is accessed or received. In one embodiment, the clinical data is accessed from the patient's electronic medical record. Current clinical data may include ICD-9 admitting diagnoses codes, working diagnoses codes, age, location, region, actual length of stay, and other clinical information such as ordered procedures, treating physicians, outcomes and other clinical data related to treatment of the patient. The predictive modeling data is applied to the current clinical data for the patient at step 306 and a predicted length of stay is calculated for the patient at step 308.

For example, the predictive modeling data may consider previously treated patients with the same ICD-9 codes that are of the same or similar age and region as the patient for which a predicted length of stay is being calculated. In another example, the predictive model may consider a wide variety of historical and current data in view of the available historical and current data for the patient and the desired objectives. For example, the time period for historical data used in the predictive model may be any time period, such as three months, six months and one year. The historical data used with the predictive model may be based on a specified region. The predictive model may also use ICD-9 codes of three, four and five digits depending on the available data.

The one or more predictive models may include a variety of statistical techniques for identifying a possible future outcome. Statistical techniques such as multiple algorithms, linear regression, partial least squares and logistic regression may be applied to stored historical data for a variety of patients. Based on the application of the predictive modeling data to the current clinical data of the patient, a predicted length of stay is calculated and stored for the patient at step 310. The predicted length of stay for the patient may be communicated or populated into a variety of databases, including a patient's electronic medical record 204 of FIG. 2.

Figure 4:
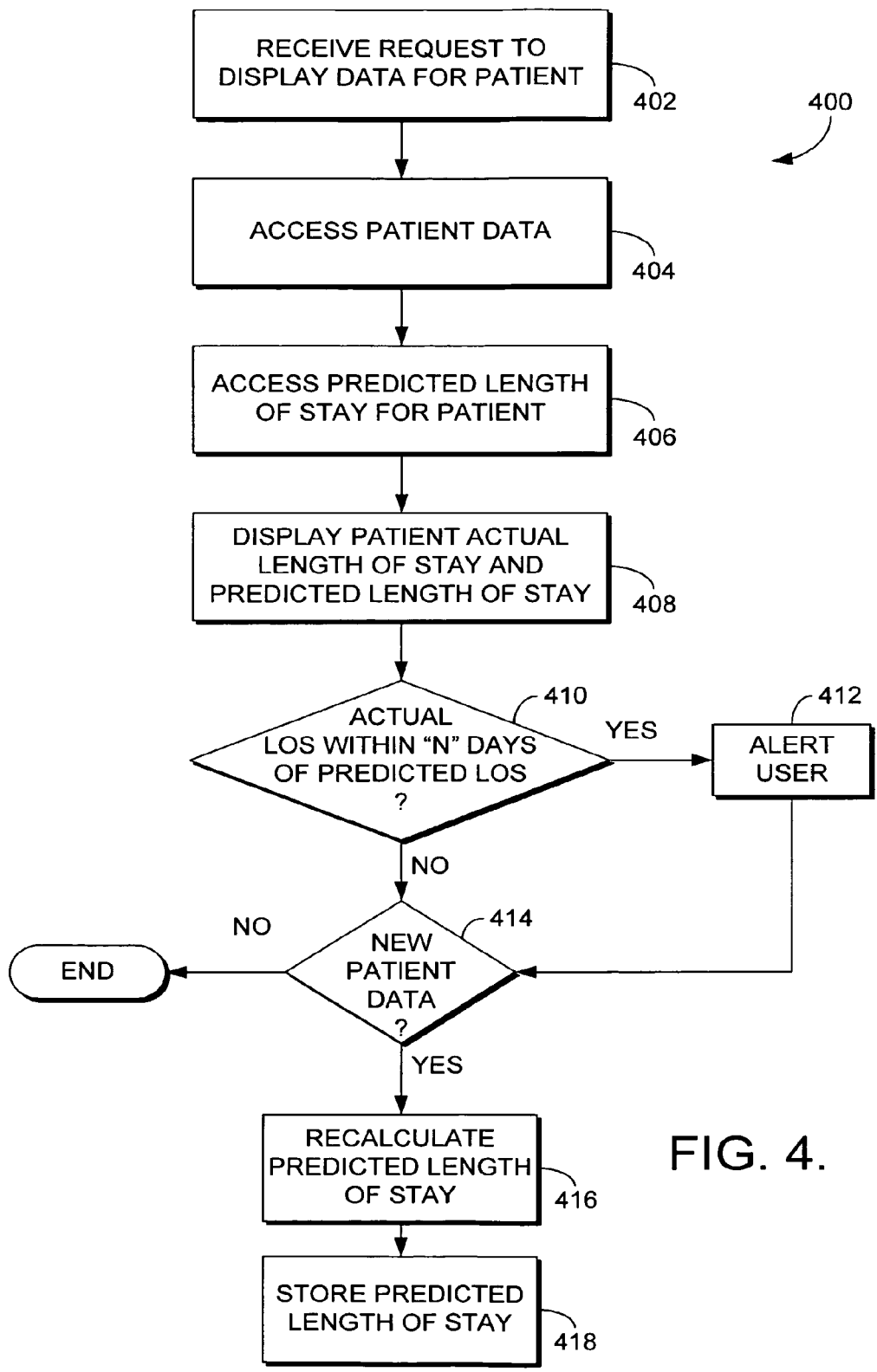
FIG. 4 is a flow diagram illustrating a method for displaying the actual length of stay and the predicted length of stay for a patient in accordance with an embodiment of the present invention.

With reference to FIG. 4, a method 400 for displaying a predicted length of stay and actual length of stay for a patient is shown. At step 402, a request to display patient data is received. For example, a case manager at a healthcare facility may request to see data for his or her patient. At step 404, patient data is accessed by accessing the patient's electronic medical record. Patient data may include patient name, identification, currently length of stay, treating physician name, admission codes, diagnosis, orders and other clinical information related to the patient's treatment. At step 406, the predicted length of stay that has been calculated and stored is accessed. The predicted length of stay may be stored in the patient's electronic medical record or other database. At step 408, the actual length of stay and the predicted length of stay for the patient are displayed.

With reference to FIG. 5, a screen 500 displaying an exemplary case manager work list is shown. The case manager work list includes the patient's name 502, the actual length of stay for the patient 504 and the predicted length of stay 506 for the patient. Exemplary patient Jane Doe has an actual length of stay of two days while her predicted length of stay calculated was three days. The actual length of stay and predicted length of stay can be displayed to a variety of users including care providers such as physicians, nurses, bed management teams, discharge planners, and case managers. Screen 500 depicts that patient names are vertically listed in a column and that each row of information aligned with a particular patient name includes other information related to the patient. For example, screen 500 also includes one or more other display areas configured to display other actual-stay values, which indicate duration of time that other patients (i.e., "Smith, John" and "Jackson, Charlie") have actually spent in a healthcare facility. In addition, screen 500 includes one or more other display areas configured to display other predicted-stay values indicating durations of time that the other patients are predicated to stay in the healthcare facility. Moreover, screen 500 includes one or more other display areas configured to display differences between the actual-stay values and the predicted-stay values. Screen 500 conveys other information as well. For example, patient names (i.e., "Doe, Jane" and "Smith, John" and "Jackson, Charlie") are vertically arranged in a ascending order from top to bottom, based on the difference for each named patient. That is, the "Diff" column illustrates that the vertical order of the patients from top to bottom is "1" and "2" and "3." As such, the top patient on the list is "Doe, Jane" having a difference of "1," which is lower than "2" and "3." By listing the patient with the lowest difference at the top of the list, the user interface suggests that "Doe, Jane" is a higher priority than the other patients.

Displaying the predicted length of stay for a patient allows a case manager to view which patients may be ready for discharge and/or determine which patients may require an extended stay for which utilization review is needed. Displaying the actual length of stay and predicted length of stay for a patient will allow a case manager to use resources efficiently and increase productivity by focusing on the patients that require priority. As such, a patient can be moved through the healthcare system to reduce the chances of complications and infections. Care can be provided to a patient that is medically necessary for cost-effective treatment. As such, the patient receives the appropriate level of care and the healthcare facility is proper reimbursed for the treatment provided.

Referring again to FIG. 4, at step 410 it is determined whether the actual length of stay is within a certain number of days (N) of the predicted length of stay. The certain number of days may be a designated number of days and may be a default of the system or for a particular user. For example, if the actual length of stay is within one day of the predicted length of stay, an alert may be provided. If at step 410 it is determined that the actual length of stay is within a certain number of days of the predicted length stay, a user is alerted at step 412 and then proceeds to step 414.

The alert may be delivered in a variety of ways including, by way of example only, an electronic mail message, adding the patient to a result queue to be viewed by a case manager, adding an alert icon or highlighting the difference of days in the case manager work list. With reference to FIG. 5, the difference in days between the predicted length of stay and actual length of stay is highlighted to alert the case manager that patient, Jane Doe's actual length of stay is within one day of the predicted length of stay.

Returning to FIG. 4, if at step 410 it is determined that the actual length of stay is not within the prescribed number of days of the predicted length of stay, at step 414 it is determined whether any new patient data has been received that would require the predicted length of stay to be recalculated. If at step 414 it is determined that new patient data has been received at step 416, the predicted length of stay for the patient is recalculated. By way of example and not by limitation, if a new ICD-9 diagnosis code for the patient is stored in the system, then the predicted length of stay for the patient may be different so recalculation of the length of stay is required. As such, at step 416, a new predicted length of stay is calculated for the patient.

At step 418, the new predicted length of stay is populated, communicated to or stored a database such as the patient's electronic medical record. In some embodiments, multiple predicted lengths of stay may be calculated for a patient during a patient's stay and each of them stored with time and date information so that they may be referred to at a later time. The recalculated predicted length of stay supercedes the current predicted length of stay for the patient, compared to the actual length of stay for the patient and displayed.

The present invention has been described in relation to particular embodiments, which are intended in all respects to illustrate rather than restrict. Alternative embodiments will become apparent to those skilled in the art that do not depart from its scope. Many alternative embodiments exist, but are not included because of the nature of this invention. A skilled programmer may develop alternative means for implementing the aforementioned improvements without departing from the scope of the present invention.

It will be understood that certain features and sub-combinations of utility may be employed without reference to features and sub-combinations and are contemplated within the scope of the claims. Furthermore, the steps performed need not be performed in the order described.

The invention claimed is:

1. A user interface embodied on one or more computer readable storage media, the user interface simultaneously displaying a predicted length of stay of one or more patients and an actual length of stay of the one or more patients currently receiving treatment in an inpatient healthcare setting, the user interface comprising:
 a first display area configured to display a first actual-stay value that indicates a number of days that a first identified patient has actually spent in an inpatient healthcare facility;
 a second display area configured to display a first predicted-stay value that indicates a number of days that the first identified patient is predicted to stay in the inpatient healthcare facility; and
 a third display area configured to display a first difference between the first actual-stay value and the first predicted-stay value,
  wherein the first difference is a value determined by subtracting the first actual-stay value from the first predicted-stay value, and
  wherein the first difference value is highlighted in the third display area when the first difference is a positive value and is one day.

2. The user interface of claim 1, further comprising:
 a fourth display area configured to display a second actual-stay value that indicates a number of days that a second identified patient has actually spent in the inpatient healthcare facility;
 a fifth display area configured to display a second predicted-stay value that indicates a number of days that the second identified patient is predicted to stay in the inpatient healthcare facility; and
 a sixth display area configured to display a difference between the second actual-stay value and the second predicted-stay value, wherein the difference is a value determined by subtracting the second actual-stay value from the second predicted-stay value.

3. The user interface of claim 2,
 wherein the user interface presents a vertically arranged listing of patients that include the first identified patient and the second identified patient and that are assigned to a case manager, and
 wherein patients listed in the vertically arranged listing of patients are listed from top to bottom in ascending order based on a respective difference of each patient, thereby suggesting a prioritization of the patients.

4. The user interface of claim 1, wherein upon determining that the first difference satisfies a prescribed threshold value and that additional patient data of the first identified patient has been received, the user interface is refreshed to present an updated predicted-stay value, which is based at least in part on the additional patient data.

5. A user interface embodied on one or more computer readable storage media, the user interface simultaneously displaying a predicted length of stay of one or more patients and an actual length of stay of the one or more patients currently receiving treatment in an inpatient healthcare setting, the user interface comprising:
 a first row of information that includes:
  (a) a first patient name,
  (b) a first actual-stay value that indicates a number of days that a first patient identified by the first patient name has actually spent in an inpatient healthcare facility,
  (c) a first predicted-stay value that indicates a number of days that the first patient is predicted to stay in the inpatient healthcare facility, and
  (d) a first difference value that includes the first actual-stay value subtracted from the first predicted-stay value; and
 a second row of information that includes:
  (e) a second patient name,
  (f) a second actual-stay value that indicates a number of days that a second patient identified by the second patient name has actually spent in an inpatient healthcare facility,
  (g) a second predicted-stay value that indicates a number of days that the second patient is predicted to stay in the inpatient healthcare facility, and
  (h) a second difference value that includes the second actual-stay value subtracted from the second predicted-stay value
   wherein the user interface presents an arranged listing of patients that include the first identified patient and the second identified patient and that are assigned to a case manager,
   wherein patients listed in the arranged listing of patients are listed from top to bottom in ascending order based on a respective difference of each patient, thereby suggesting a prioritization of the patients, and
   wherein the first difference value is highlighted when the first difference value is a positive value and is one day.

6. The user interface of claim 5, wherein upon determining that the first difference value is one day and that additional patient data of the first patient has been received, the user interface is refreshed to present an updated predicted-stay value of the first patient, which is based at least in part on the additional patient data.

7. A user interface embodied on one or more computer readable storage media, the user interface simultaneously displaying a predicted length of stay of one or more patients and an actual length of stay of the one or more patients currently receiving treatment in an inpatient healthcare setting, the user interface comprising:
 one or more portions that present:
  a patient name;
  an actual-stay value that indicates a number of days that a patient identified by the patient name has actually spent in an inpatient healthcare facility;

a predicted-stay value that indicates a number of days that the patient is predicted to stay in the inpatient healthcare facility; and a difference value that includes the actual-stay value subtracted from the predicted-stay value, wherein upon determining that the difference is a positive value and is one day and that additional patient data of the patient has been received, an updated predicted-stay value is calculated based on the additional patient data and the user interface is refreshed to present the updated predicted-stay value of the patient.

* * * * *